(12) United States Patent
Marzok et al.

(10) Patent No.: US 12,167,868 B1
(45) Date of Patent: Dec. 17, 2024

(54) ENUCLEATION-EXENTERATION APPROACH OF THE CAMEL EYE VIA THE SUPRAORBITAL FOSSA

(71) Applicant: King Faisal University, Al-Ahsa (SA)

(72) Inventors: Mohamed Abdlmoniem Abdelmaksoud Marzok, Al-Hofouf (SA); Adel Ibrahim Almubarak, Al-Hofouf (SA); Mahmoud Kandeel Elsayed, Al-Hofouf (SA); Mohamed Ahmed Nazih, Cairo (EG); Mohamed Tawik El-Sherif, El Mahalla el Kubra (EG)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/427,387

(22) Filed: Jan. 30, 2024

(51) Int. Cl.
| | | |
|---|---|---|
| *A61B 17/3209* | (2006.01) | |
| *A61B 17/32* | (2006.01) | |
| *A61D 99/00* | (2006.01) | |
| *A61F 9/007* | (2006.01) | |

(52) U.S. Cl.
CPC .......... *A61B 17/3209* (2013.01); *A61D 99/00* (2013.01); *A61F 9/007* (2013.01); *A61B 2017/320044* (2013.01)

(58) Field of Classification Search
CPC ............... A61B 17/00; A61B 17/3209; A61B 17/32093; A61B 2017/320044; A61D 1/00; A61D 99/00; A61F 9/007; A61F 9/00709; A61F 9/00736
See application file for complete search history.

(56) References Cited

U.S. PATENT DOCUMENTS

2019/0133930 A1   5/2019   Mulvahill

FOREIGN PATENT DOCUMENTS

| RU | 2261071 C1 * | 9/2005 |
| RU | 2550285 C1 * | 5/2015 |
| RU | 2662415 C1 * | 7/2018 |

OTHER PUBLICATIONS

Hanada et. al., Combined Transcranial-supraorbital and Transconjunctival Approach for Optic Nerve Coloboma with Ophthalmic Dysplasia Associated with Rheumatoid Arthritis, NMC Case Report Journal, 2020, DOI : https://doi.org/10.2176/nmccrj.cr.2018-0302.
Mitchell, "Enucleation in companion animals", Irish Veterinary Journal, vol. 61, No. 2, Dec. 2008.
Kowanz et al., "Evisceration, enucleation and exenteration-Indications, techniques, and postoperative care", Ophthalmologie. Feb. 2023;120(2):126-138. German. doi: 10.1007/s00347-022-01791-4. Epub Jan. 12, 2023. PMID: 36635593.

* cited by examiner

*Primary Examiner* — Robert A Lynch
(74) *Attorney, Agent, or Firm* — Nath, Goldberg & Meyer; Joshua B. Goldberg (57) ABSTRACT

A method for removing an eye and ocular structures through a supraorbital fossa in a camel is disclosed herein, the method comprising: making a U-shaped incision along a supraorbital fossa of the camel; dissecting one or more tissues surrounding the supraorbital nerve in the camel; and removing eye globe and surrounding tissues through the supraorbital fossa.

10 Claims, 9 Drawing Sheets

ENUCLEATION-EXENTERATION APPROACH OF THE CAMEL EYE VIA THE SUPRAORBITAL FOSSA

BACKGROUND

1. Field

The disclosure of the present patent application relates to a surgical method and, particularly, to a removal of a camel's eye through the supraorbital fossa.

2. Description of the Related Art

The current, most widely used method for performing enucleation-exenteration eye removal on a camel is to cut incisions around or under the eyelids, or the conjunctiva of the camel. This current method involves dissecting down to the eyeball of the camel. This approach creates a lot of tissue damage and bleeding. This current method is a blind method and does not easily allow full removal of the orbital content. This can make it more difficult to fully remove tumors and other diseased tissue, particularly those involving periorbital soft tissue and bone masses Thus, a new surgical method that decreases these challenges is desired.

SUMMARY

The present subject matter relates to a surgical method for the removal of a camel's eyeball and/or surrounding tissue through the supraorbital fossa. This new method offers a wide and direct open surgical field visualization and minimizing tissue damage and bleeding.

A method for removing an eye of a camel and ocular structure through the supraorbital fossa in a camel comprises: making a U-shaped incision along a supraorbital fossa of the camel; dissecting one or more tissues surrounding the supraorbital nerve in the camel; and removing an eye globe and surrounding tissues through the supraorbital fossa.

In certain embodiments, the present methods may further include pulling back a skin flap formed by the U-shaped incision to expose tissue under the skin flap. The present methods may also include not removing the eye globe and surrounding tissues through the orbit in a frontal bone of the camel. The present methods may also include dissecting one or more tissues by blunt dissection using blunt instruments. The present methods may also include dissecting one or more tissues by blunt dissection using hands of a surgeon. The present methods may further include replacing the skin flap and stitching the skin flap.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as disorders of the eye, including tumors and other ailments.

Enucleation-Exenteration: Enucleation-exenteration, as referenced in patent document, typically denotes a surgical procedure involving the removal of the eye and related structures. This procedure is commonly employed for therapeutic or diagnostic purposes in cases of severe ocular or orbital pathology.

Supraorbital fossa: The supraorbital fossa in animals refers to a bony depression or hollow space located above the eye socket (orbit) on the skull. This anatomical feature is commonly observed in various species, especially equine and camel, serving as a region where muscles, nerves, and blood vessels associated with the eye and forehead are accommodated. The size and structure of the supraorbital fossa can vary among different animal species, the largest size in camel.

Orbit and orbital cavity: The orbit refers to the bony socket in the skull that houses and protects the eyeball. It is also known as the eye socket. The orbit is composed of several bones, including the frontal bone, zygomatic bone, maxilla, palatine bone, ethmoid bone, lacrimal bone, and sphenoid bone. Together, these bones create a protective cavity that surrounds and supports the eye.

The orbital cavity is the hollow space within the orbit that accommodates the eyeball and associated structures such as muscles, nerves, blood vessels, and connective tissues. The orbital cavity plays a crucial role in maintaining the position and protection of the eye while allowing for various movements and functions.

Conjunctiva: The conjunctiva is a thin, transparent mucous membrane that covers the front surface of the eye (excluding the cornea) and lines the inner surface of the eyelids. It serves to protect and lubricate the eye by producing mucus and tears. The conjunctiva also plays a role in preventing microorganisms and foreign particles from entering the eye.

Dissection: A technique involving the careful separation and examination of the components of a biological specimen, typically an animal tissue, to better understand its anatomical structure or perform surgery.

Fascia: Refers to a connective tissue that forms a three-dimensional web throughout the body, providing support, structure, and a framework for various organs and tissues.

Periorbital: Periorbital refers to the area surrounding the orbit or eye socket.

The anatomical structure and characteristics of camels require a tailored approach for various surgeries and treatments, particularly surgery of the camel cranium. Camels possess unique cranial features, such as a prominent supraorbital fossa, which necessitate a specific incision pattern. A U-shaped incision as described herein may allow for precise access to the orbital contents while minimizing the risk of damage or disruption to surrounding tissues. The U-shaped incision technique in camels may provide enhanced surgical visibility and maneuverability compared to other surgical approaches utilized in different species. The meticulous dissection of surrounding tissues may allow for optimal visualization and control during the procedure, ensuring the safety and successful outcome of the operation. Moreover, this technique may also allow for more reliable application and fixation of prostheses, which may lead to better cosmetic outcomes. Also, the supraorbital technique has been shown to be less hemorrhagic, which may reduce the risk of postoperative complications.

Figure 1:
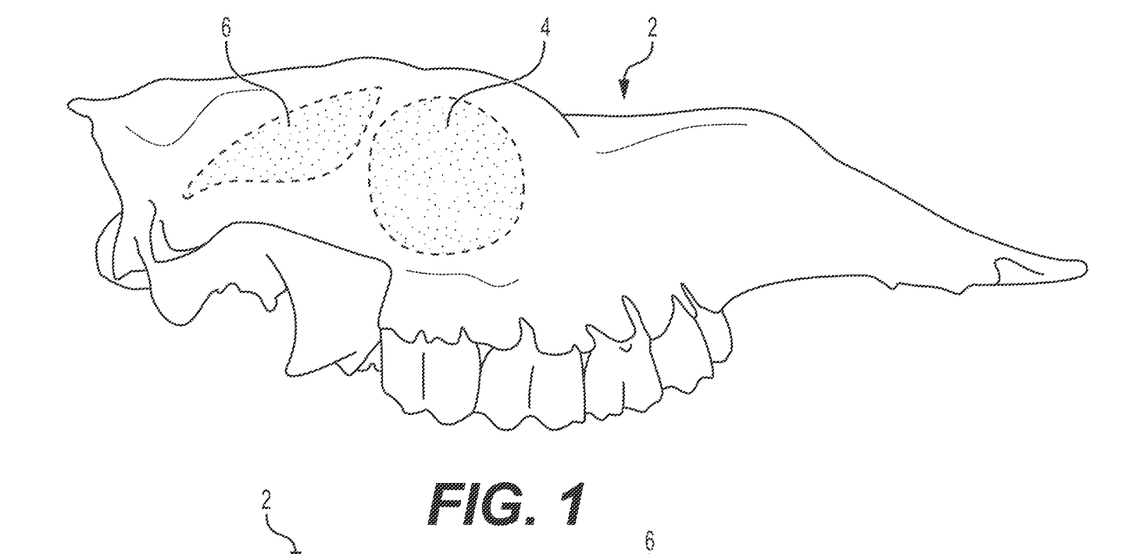
FIG. 1 shows a side view of a camel skull hightlighting the ventral lateral orbital cavity and the supraorbital fossa.
Figure 2:
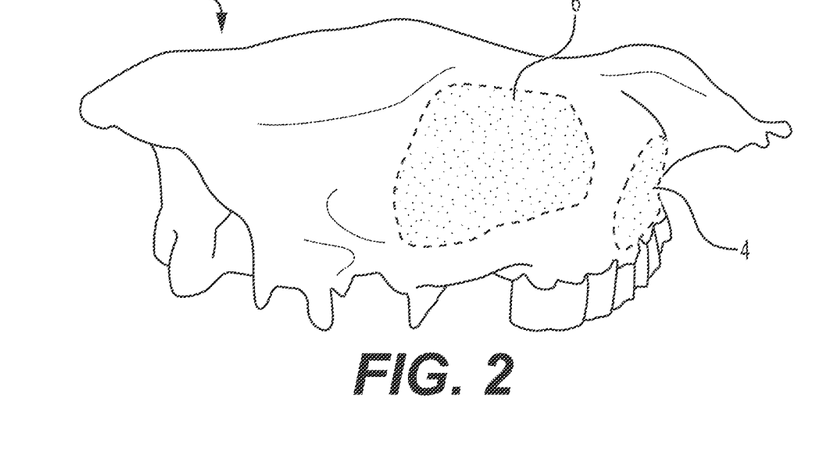
FIG. 2 shows a dorsal view of the camel skull, emphasizing the orbital cavity and supraorbital fossa.

Referring to FIGS. 1-2, skull 2 of a camel is illustrated. FIG. 1 illustrates a side view of the camel skull 2. As illustrated, the camel skull includes a ventral lateral orbital fossa 4 and supraorbital fossa 6. In FIG. 2, a dorsal view of the camel skull 2 is illustrated. In this view, the large size of the supraorbital fossa 6 is illustrated. The supraorbital fossa 6 is a depression located above the orbit (eye socket) in the frontal bone of the camel skull 2. In veterinary anatomy, this region plays a role in housing various structures, including nerves, blood vessels and a back entry to the orbital cavity and the eyeball. In most enucleation-exenteration surgeries, the eye of the subject is accessed through the ventral lateral orbital. However, the camel has a larger supraorbital fossa 6 than found in other species and this larger size allows for an alternative method for removal of an eye of a camel as will be described herein.

Prior methods for enucleation in camels involved making an incision along the eyelids or conjunctiva and dissecting down to the eyeball. This approach creates more trauma and bleeding compared to the technique presented herein.

Figure 3:
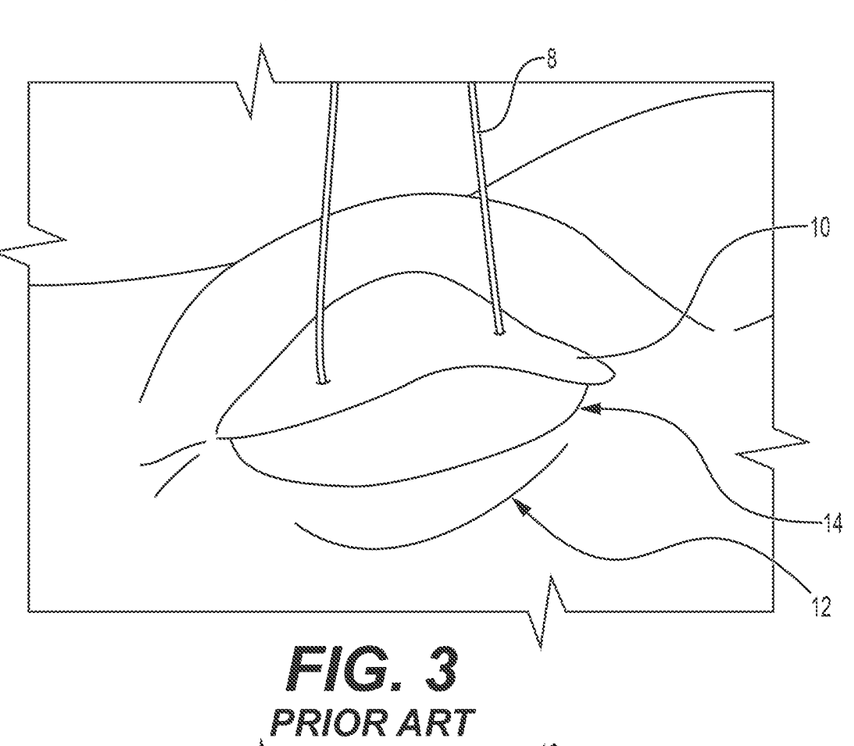
FIGS. 3, 4, 5, and 6 each illustrate certain features of the prior art method of performing surgery on the orbital cavity of a camel where the eyeball is extracted through the rostral entry of the orbital cavity.
Figure 4:
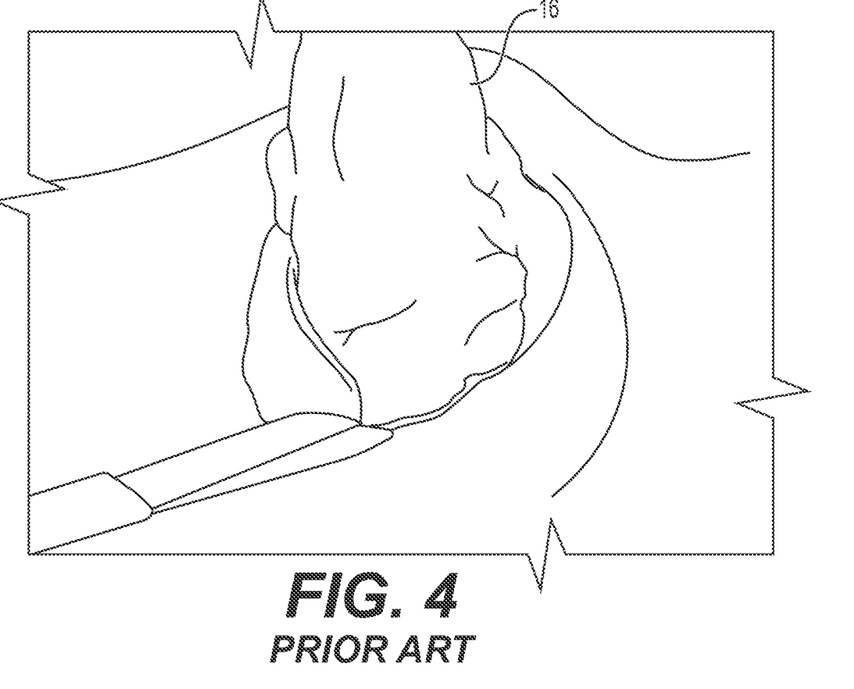
Figure 5:
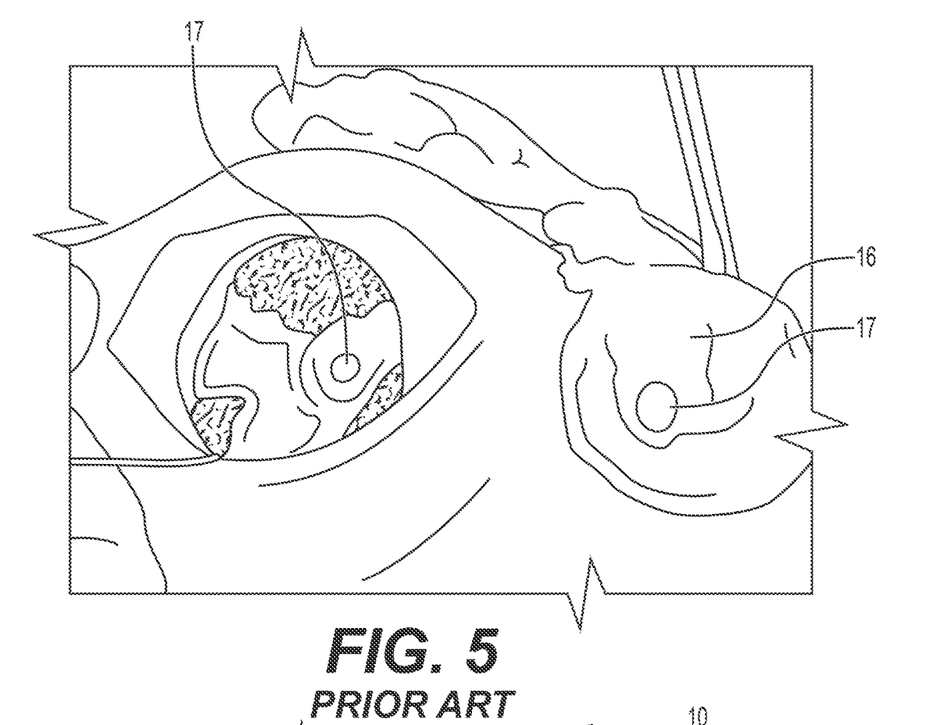
Figure 6:
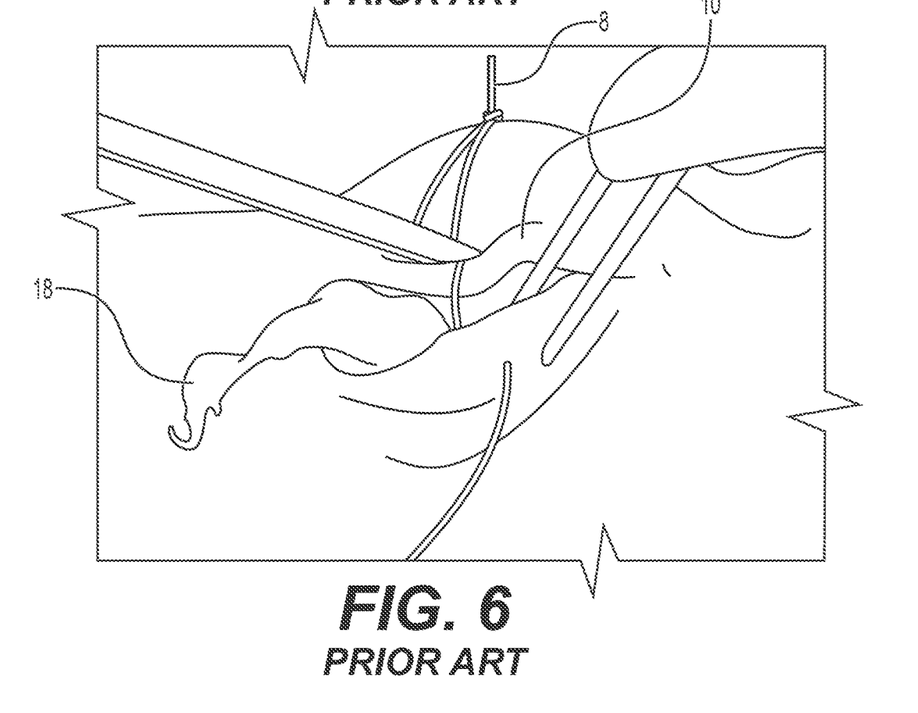

Referring to FIGS. 3-6, a prior art method of enucleation-exenteration surgery in a camel is illustrated. FIG. 3 illustrates the eyelids 10 being sutured together with simple continuous sutures 8 using silk or any other non-absorbable suture material. The ends of the suture are kept longer and tied together to make a loop for handling, continued traction and stabilizing the globe of the eye (or eyeball) during dissection. An incision 12 is then made below the palpebral border of the lower eyelid 14. An additional incision is made above the palpebral border of the upper eyelid. In FIG. 4, the orbital muscles and connective tissue are dissected through until the orbital stump 16 is reached. In FIG. 5, the orbital stump 16 having been severed is illustrated. The optical nerve is illustrated 17. Finally in FIG. 6, the eyelids 10 are sutured shut after packing the opening with gauze 18. The gauze is removed bit by bit over the course of days.

The present methods as described herein may provide better visualization of the orbital cavity contents as prior art methods are considered blind techniques. The new method for removing performing eye surgery on a camel may provide better hemorrhage control. The new method may also allow for better instrument and tissue manipulation. The method described herein can allow for complete removal of the orbital content, especially when deep tumors are present. The new method may also give a more appealing cosmetic appearance and increased feasibility of prosthetic eye implantation.

Figure 7:
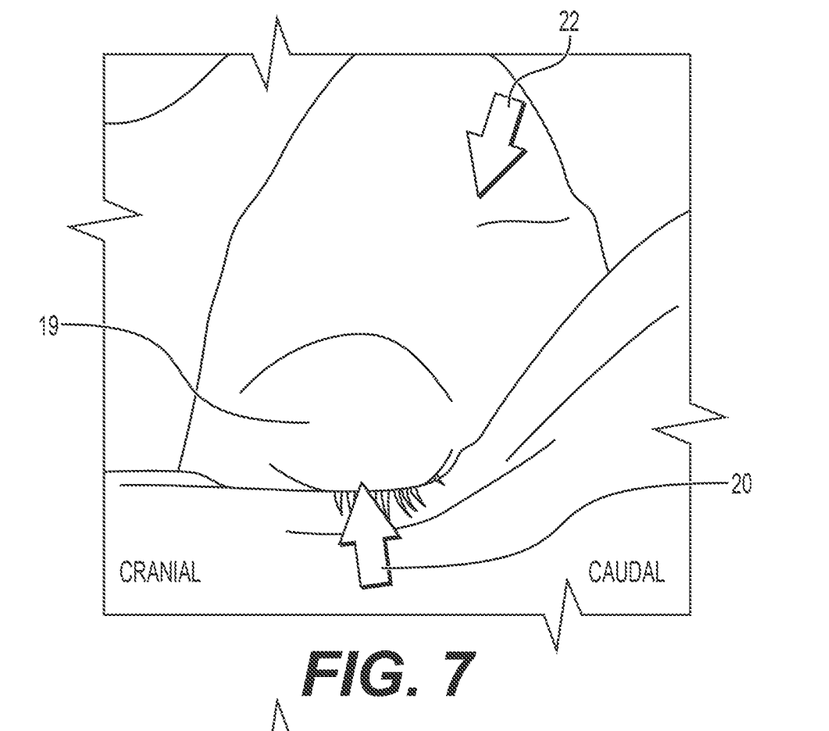
FIG. 7 illustrates the position of an eye of a camel where both the orbital fossa and supraorbital fossa are accessible.
Figure 8:
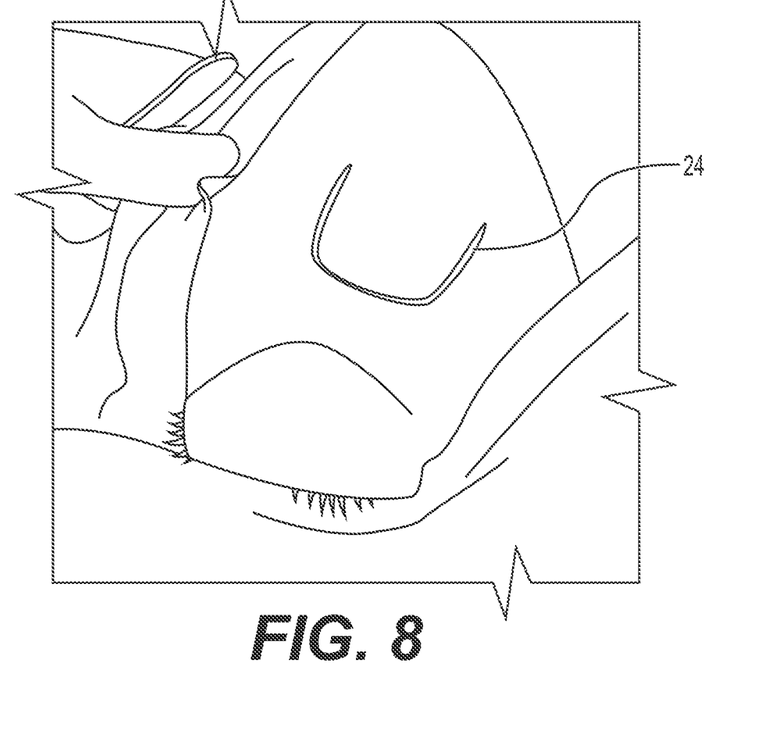
FIG. 8 illustrates an implementation of a U-shaped incision in the skin of the supraorbital fossa of a camel.

Referring to FIGS. 7-18, an implementation of a method for removing a supraorbital nerve in a camel is illustrated. In FIG. 7, the position of an eye of a camel is illustrated 19. In this view, both the orbital fossa 20 and supraorbital fossa 22 are accessible. The method includes making a U-shaped 24, or semi-circular, incision along a supraorbital fossa of the camel as illustrated in FIG. 8. The semi-circular design of the incision conforms precisely to the camel's natural orbital anatomy, avoiding risks associated with a straight incision performed in prior art methods. The risks can include damage to the prominent orbital ridge of the camel's skull. The U-shaped incision 24 may important surgical advantages over previous methods for camel enucleation.

Figure 9:
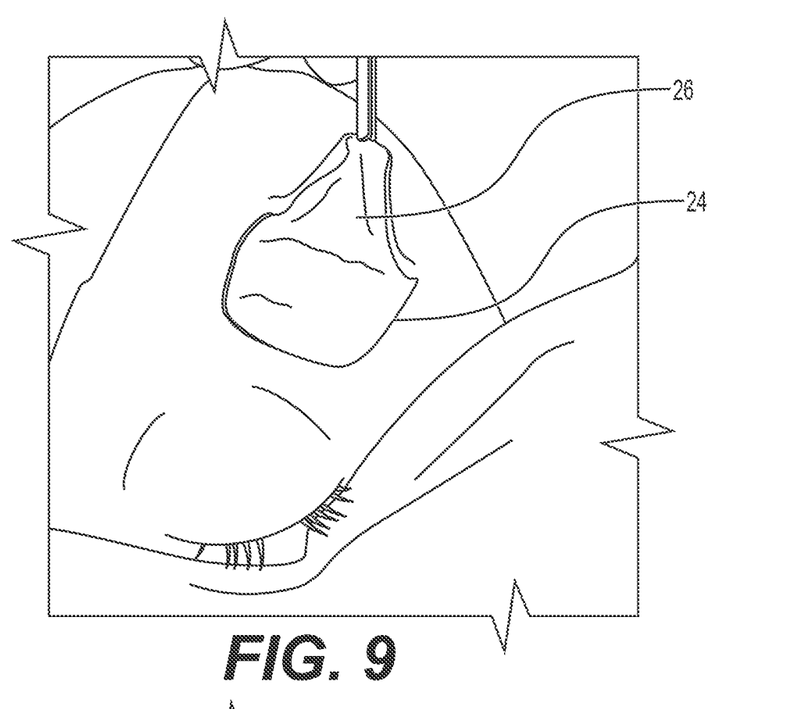
FIG. 9 illustrates an implementation of a surgical window through a dissected skin flap of a camel, which is pulled away subsequent to the U-shaped incision in the skin and fascia.
Figure 10:
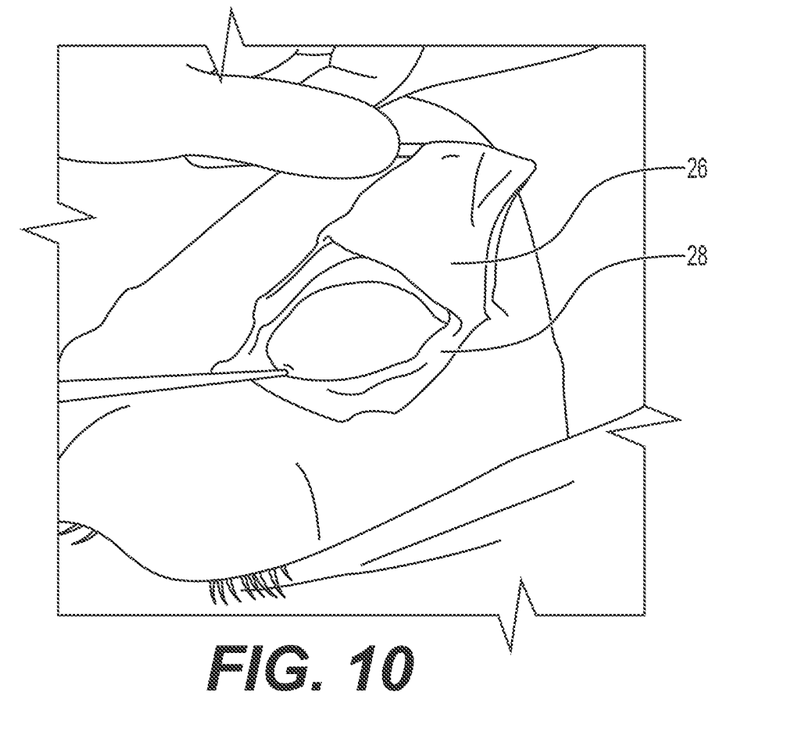
FIGS. 10, 11, and 12 each illustrate certain features of sharp and blunt dissection of tissues surrounding the eye globe of a camel.
Figure 11:
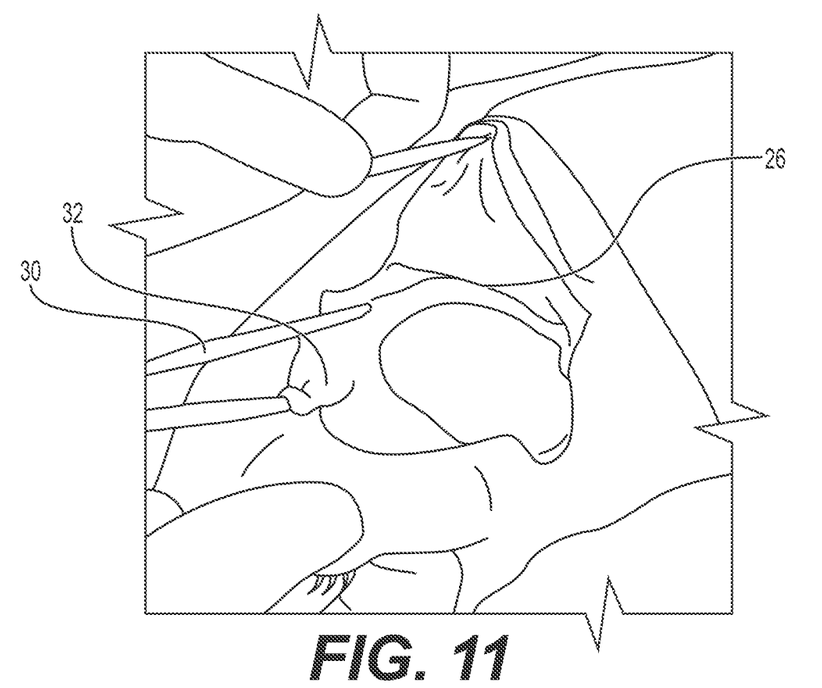
Figure 12:
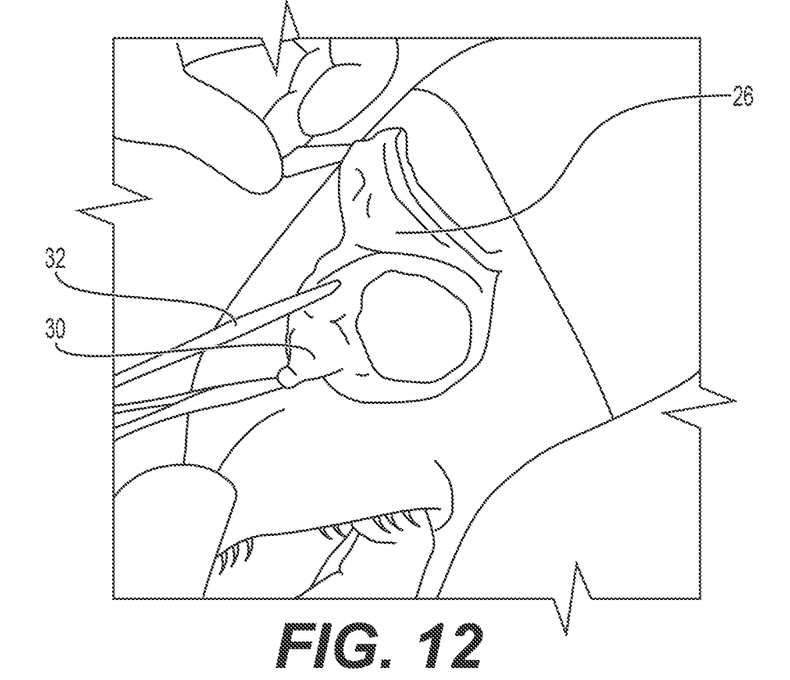
Figure 13:
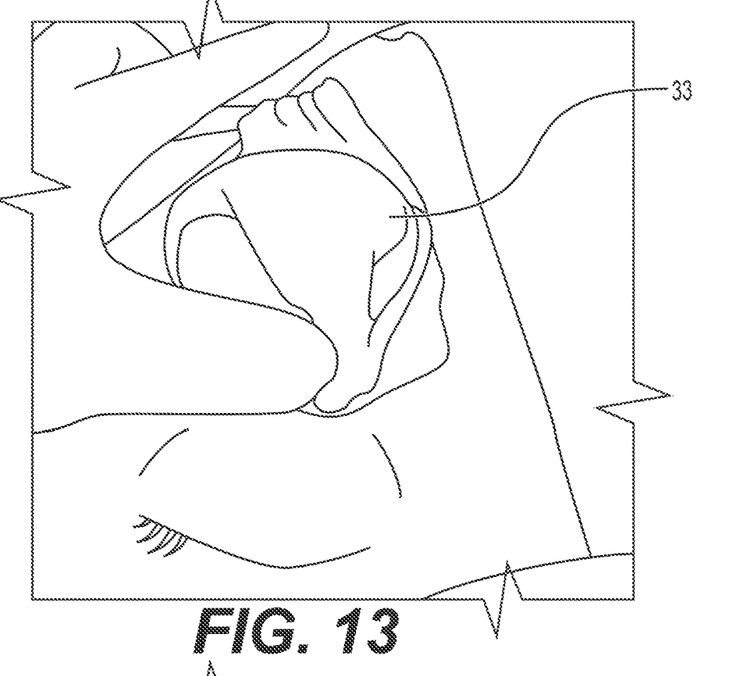
FIGS. 13, 14, and 15 each illustrate certain features of removal of the eye globe, periorbital fat and muscular cone of the eye and optic nerve of a camel through the created supraorbital window.

The method further includes pulling a skin flap 26 back formed by the U-shaped 24 incision as illustrated in FIG. 9. Pulling the skin flap 26 back exposes the tissue under the skin flap 26. The method also includes dissecting one or more outer tissues to gain access to the orbital contents 28 as illustrated in FIG. 10. The method then includes dissecting one or more tissues 30 surrounding the supraorbital nerve in the camel as illustrated in FIGS. 11-12. The dissecting of the one or more tissues surrounding the supraorbital nerve may include blunt dissection. In various embodiments, blunt dissection may be performed by instruments 32 as illustrated in FIGS. 11-12. In various embodiments, the instruments may include scissors, tweezers, or any other instruments that have a rounded or blunted end. In other embodiments, blunt dissection may be performed by the hands of a surgeon or other person involved in the surgery.

Figure 14:
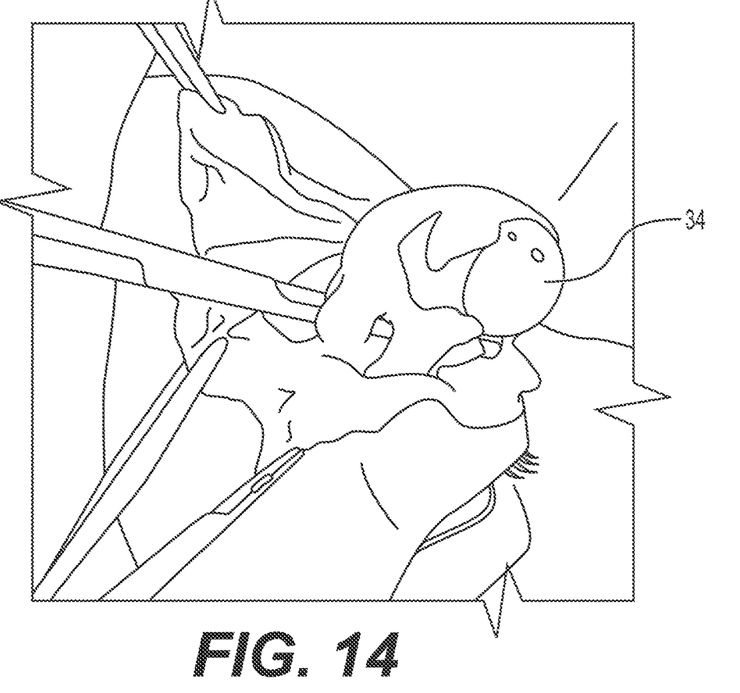
Figure 15:
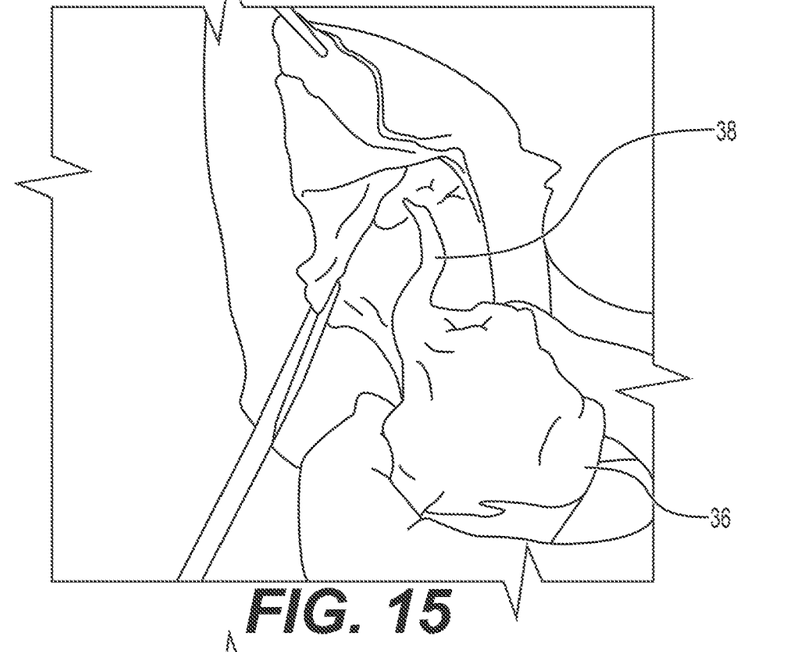

The present methods can further include removing the eye globe, or eyeball, through the supraorbital fossa 22. Removal of the eye globe 34 is illustrated in FIGS. 14 and 15. The method can also include removing the tissues 33 and 36 surrounding the eye globe 34, including but not limited to the optical nerve 38. The method can include removing the eye globe 34 and surrounding tissue 33, 36 through the supraorbital fossa 22 and not through the orbit in the frontal bone of the camel.

Figure 16:
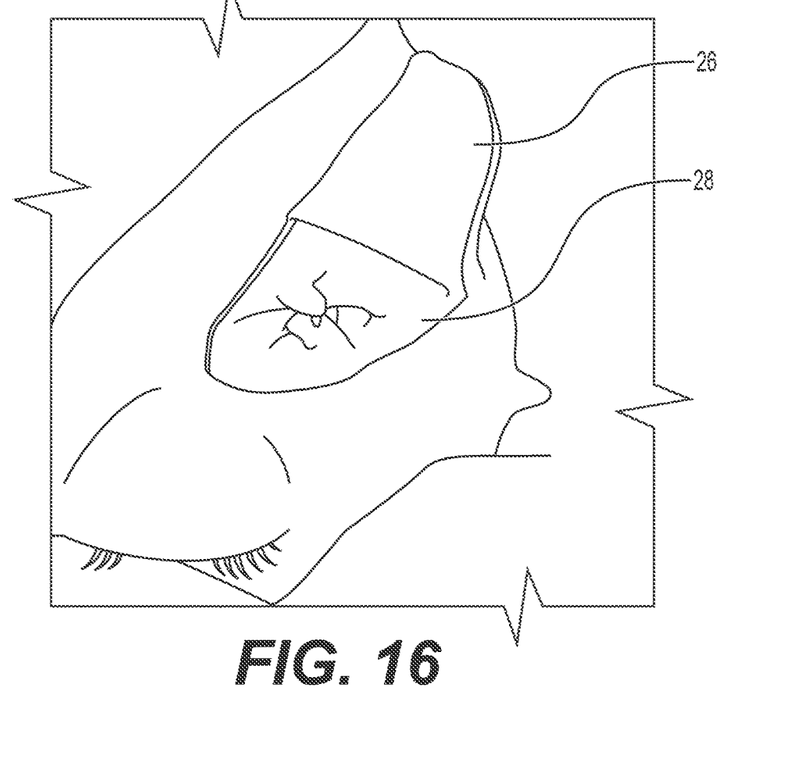
FIG. 16 illustrates the incision site after removal of the eye globe of a camel.
Figure 17:
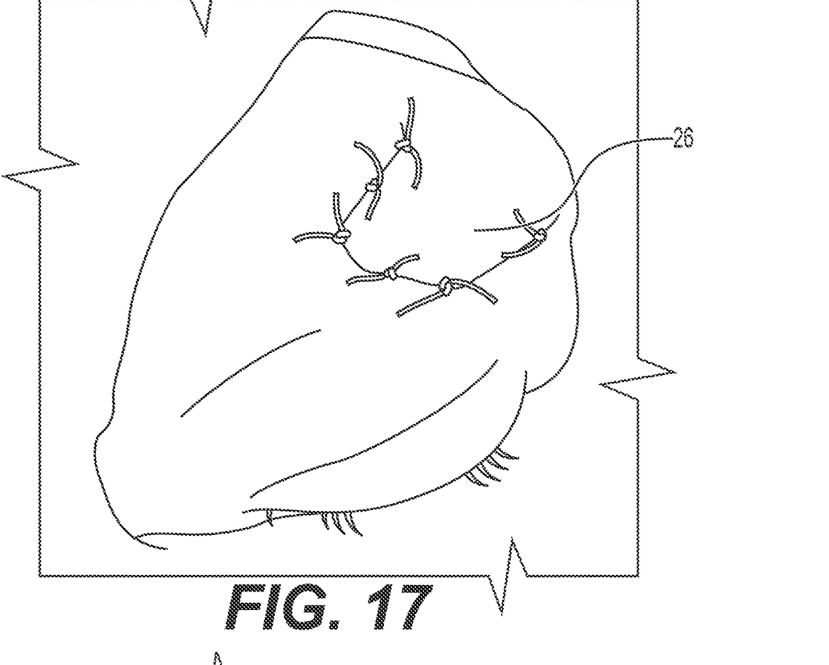
FIG. 17 illustrates reduction and suturing of the skin flap back to its normal position in the supraorbital fossa of a camel.
Figure 18:
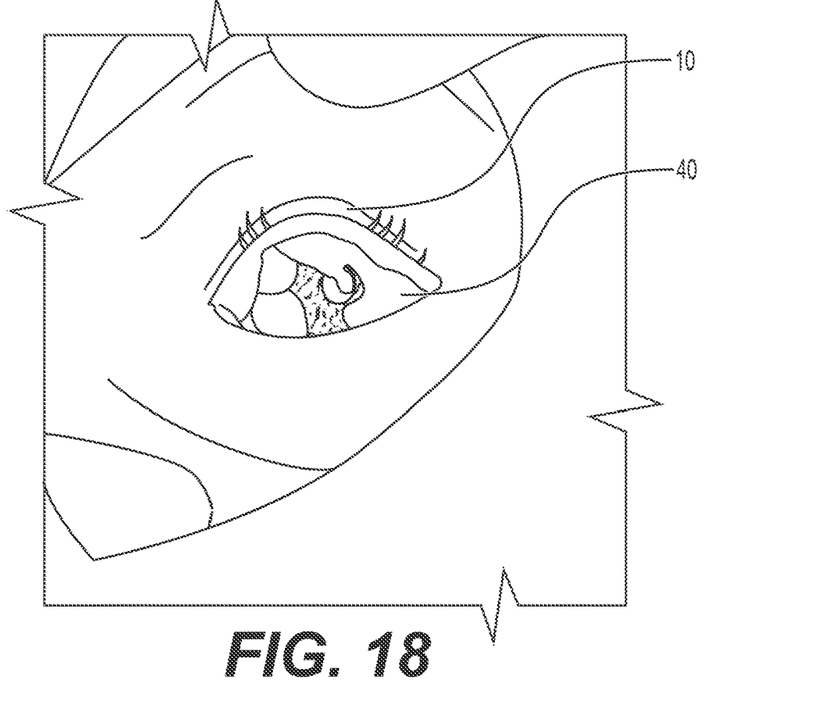
FIG. 18 illustrates an empty optical cavity and intact eyelids of a camel after the removal of the eye globe through the supraorbital fossa of the camel using an implementation of a surgical method as described herein.

Finally, the method can include suturing the outer tissue 28 of the orbital fossa 20 as illustrated in FIG. 16. The skin flap 26 can then be placed back into its original position and stitched into place. As illustrated in FIG. 18, the eyelid 10 can be opened to view the empty eye socket 40.

The unique anatomical characteristics of camels proposed application of modified approaches for various surgical procedures, especially those involving the camel eye. Notably, camels exhibit distinctive orbital features, including a large size, prominent supraorbital fossa. The application of a U-shaped incision in the supraorbital fossa with subsequent dissection of the fascia creating a surgical window, as detailed in this context, offers precise access to orbital contents while minimizing the potential for bleeding or damage to eyelids. The access through the supraorbital fossa provides heightened surgical visibility and maneuverability compared to approaches employed through eyelid (palpebral) or subconjunctival techniques. The current novel surgical approach offers diligent dissection of ocular tissues ensures optimal visualization and control, increasing the safety and success rate of the procedure. Additionally, this technique facilitates more reliable application and fixation of prostheses especially with the presence of intact eyelids, contributing to improved cosmetic outcomes. Furthermore, the supraorbital technique demonstrates reduced intraoperative complications such as bleeding, thereby mitigating the risk of postoperative complications.

The utilization of the supraorbital enucleation-exenteration method described herein may minimize risk of injury to the optical nerve and surrounding vital structures thereby reducing potential complications associated with traditional enucleation-exenteration techniques. The improved visibility of the supraorbital approach may allow for more accurate tissue removal. This may ensure complete eradication of diseased or affected tissue. The supraorbital method may also reduce surgical time which contributes to faster recovery periods and enhanced post-operative outcomes for the animal.

It is to be understood that the method of enucleation-exenteration described herein are not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for removing an eye and ocular structures through a supraorbital fossa in a camel, the method comprising:
    making a U-shaped incision along a supraorbital fossa of the camel;
    dissecting one or more tissues surrounding the supraorbital nerve in the camel; and
    removing an eye globe and surrounding tissues through the supraorbital fossa of the camel.

2. The method of claim 1, further comprising pulling a skin flap back formed by the U-shaped incision to expose tissue under the skin flap.

3. The method of claim 2, further comprising replacing the skin flap and stitching the skin flap.

4. The method of claim 1, wherein the eye globe and surrounding tissues are not removed through an orbit in a frontal bone of the camel.

5. The method of claim 1, wherein the dissecting one or more tissues comprises blunt dissecting using blunt instruments.

6. The method of claim 1, wherein the dissecting one or more tissues comprises blunt dissecting using hands of a surgeon.

7. A method for removing a supraorbital nerve in a camel, the method comprising:
- making a U-shaped incision along a supraorbital fossa of the camel;
- pulling a skin flap back formed by the U-shaped incision to expose tissue under the skin flap;
- dissecting one or more tissues surrounding the supraorbital nerve in the camel;
- removing an eye globe and surrounding tissues through the supraorbital fossa of the camel;
- replacing the skin flap; and
- stitching the skin flap.

8. The method of claim 7, wherein the eye globe and surrounding tissues are not removed through an orbit in a frontal bone of the camel.

9. The method of claim 7, wherein the dissecting one or more tissues comprises blunt dissecting using blunt instruments.

10. The method of claim 7, wherein the dissecting one or more tissues comprises blunt dissecting using hands of a surgeon.

* * * * *